United States Patent [19]

Wynne et al.

[11] 4,131,609
[45] Dec. 26, 1978

[54] SILICON-PHTHALOCYANINE-SILOXY MONOMERS

[75] Inventors: Kenneth J. Wynne, Falls Church, Va.; John B. Davison, Amherst, N.Y.

[73] Assignee: The United States of America as represented by the Secretary of the Navy

[21] Appl. No.: 880,515

[22] Filed: Feb. 23, 1978

[51] Int. Cl.$^2$ .............................................. C09B 47/04
[52] U.S. Cl. .............................. 260/314.5; 260/326.8; 528/11; 528/37; 528/40; 260/37 R
[58] Field of Search ...................................... 260/314.5

[56] References Cited

U.S. PATENT DOCUMENTS 3,996,196  12/1976  D'Alelio .......................... 260/47 CP

OTHER PUBLICATIONS

Davison, et al., Research Report from the Polymeric Materials Branch, Chemistry Division, Naval Research Laboratory, Washington, D.C. 20375, 20 pp. and 5 pp. dwgs etc.

Esposito et al., Inorg. Chem. vol. 5, pp. 1979 to 1983 (1966).

Primary Examiner—John D. Randolph
Attorney, Agent, or Firm—R. S. Sciascia; Philip Schneider; Thomas McDonnell

[57] ABSTRACT

A silicon-phthalocyanine-siloxy monomer having the formula:

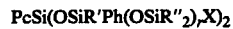

wherein X is a hydroxyl group or unreido group having the formula:

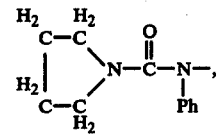

Pc is a phthalocyanine nucleus, R' and R" are alkyl groups having from 1 to 8 carbon atoms, and r is an integer from 1 to 4. The monomers are useful as dyes and in polymer synthesis as reactive intermediates.

6 Claims, No Drawings

SILICON-PHTHALOCYANINE-SILOXY MONOMERS

BACKGROUND OF THE INVENTION

The present invention pertains generally to inorganic monomer synthesis and particularly to inorganic phthalocyanine silicon monomers.

The importance of siloxy-monomers is increasing because of expanding interest in modifying siloxane polymers. For example, monomers containing phenylene and carborane moieties have been reported to impart to siloxane polymers improved thermal stability and/or resistance to reversion reactions when incorporated into the polymer backbone. A siliconphthalocyanine-siloxy monomer would be valuable because this monomer would provide means for including the phthalocyanine nucleus into the polymer structure. Such a monomer would have extremely high thermal stability and intense color. If the monomer would further contain reactive Si—OH groups, it would be versatile in polymer synthesis. If the monomer has ureido groups instead of hydroxyl groups, high reactivity would be imparted to the monomer. Such monomers would be particularly useful as dyes, reactive surface modifiers or coating agents, intermediates in polymer synthesis, and chain extenders for hydroxyl-terminated polymers. Unfortunately most phthalocyanine compounds are extremely insoluble which prevents the addition of reactive groups and prevents the utilization of these compounds for the modification of polymer properties.

SUMMARY OF THE INVENTION

It is, therefore, an object of this invention to synthesize highly soluble phthalocyanine-siloxy monomers.

A further object is to provide highly reactive phthalocyanine-siloxy monomers suitable for incorporation of phthalocyanine-siloxane units into polymers.

Another object of this invention is to provide a novel class of thermally stable dyes and reactive surface modifying agents.

These and other objects are achieved by siliconphthalocyanine-siloxy-monomers having hydroxyl or ureido groups and a reduced monomer lattice energy which enhances solubility.

DETAILED DESCRIPTION OF THE INVENTION

The monomers of the present invention have the structural formula:

wherein Z is $[-OSiR'Ph(OSiR_2'')_rX]$; X is a hydroxyl or ureido group; r is an integer from 1 to 4; and Ph is a phenyl group.

The synthesis and experimental results are reported in detail in Davison, John B. and Wynne, Kenneth J., *Silicon-Phthalocyanine Siloxane Polymers: Synthesis and $^1H$ Nuclear Magnetic Resonance Study.* U.S. Navy Technical Report, No. 1, ONR Control N00014-75-C-0693, Mar. 1977. This report is incorporated by reference herein. The synthesis of these silicon-phthalocyanine-siloxy monomers is now shown schematically. In the equations, Pc represents a phthalocyanine nucleus, Ph represents a phenyl group, Ur represents a ureido group having the formula:

py represents pyridine.

$$PcSiCl_2 + 2\,NaOH \longrightarrow PcSi(OH)_2 + 2\,NaCl \qquad (1)$$
$$(A) \qquad\qquad\qquad (B)$$

$$PcSi(OH)_2 + 2R'PhSiCl_2 + 2py \longrightarrow \qquad (2)$$
$$(B)$$
$$PcSi(OSiR'PhCl)_2 + 2pyHCl$$
$$(C)$$

$$PcSi(OSiR'PhCl)_2 + 2H_2O \longrightarrow \qquad (3)$$
$$(C)$$
$$PcSi(OSiR'PhOH)_2 + 2\,HCl$$
$$(D)$$

The oxysilicon substituent to the phthalocyanine silicon of the phthalocyanine-siloxane disilanol may be extended to include additional oxyalkylsilicon units, which increase the solubility of the compound.

Overall the practical upper limit of the oxyalkylsilicon units appears to be three, but four would be useful if exceptionally high solubility were desired. The preparation of phthalocyanine disilanols is now schematically shown.

$$PcSi(OSiR^1PhOH)_2 + 2R^2_2SiCl_2 + 2py \longrightarrow \qquad (4)$$
$$(D)$$
$$PcSi(OSiR^1PhOSiR^2_2Cl)_2 + 2pyHCl$$
$$(E)$$

$$PcSi(OSiR^1PhOSiR^2_2Cl)_2 + H_2O \longrightarrow \qquad (5)$$
$$(E)$$
$$PcSi(OSiR^1PhOSiR^2_2OH)_2 + 2HCl$$
$$(F)$$

As reactions (4) and (5) are repeated, additional units are added. Alternatively a terminally chloro-substituted di-ortrisiloxane may be used in step (4) to achieve longer siloxy chains more efficiently. The disilanols so obtained may be represented as:

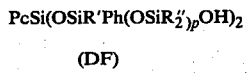

(DF)

wherein p is an integer from 0 to 4. The preferred disilanols are those with p equal 0 or 1, which are compounds D and F respectively.

The above disilanols are reacted with a bis(ureido) silane or siloxane comonomers having the formula $UrR_2^3Si(OSiR_2^4)_qUr$ to obtain the ureido containing monomers this invention. The ureido silanes or siloxanes are prepared by the method disclosed in Hedaya, et al. in *J. Polym. Sci. Polym. Chem.*, 15, p. 2229, (1977). This reaction is now schematically shown.

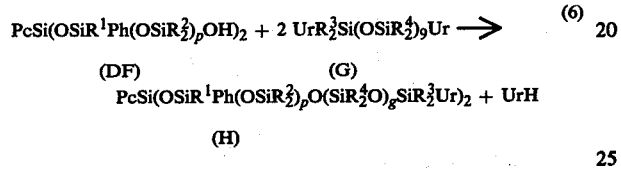

Formula H may be rewritten as:

where r is an integer from 1 to 4 (r equals p + q + 1) and preferably 1 or 2, R' and R'' are alkyls having from 1 to 8 carbon atoms and preferably are the methyl, ethyl, and propyl groups.

Having described the invention generally, the following examples are given to demonstrate the preparation of the comonomers of this invention. It is understood that these examples are given by way of illustration and are not meant to limit the disclosure or the claims to follow.

The ir (infrared) spectra of all compounds were recorded in KBr pressed pellets on a Perkin Elmer Model 467 spectrometer. The proton nmr spectra were recorded on a JEOLCO PS-100 spectrometer. Samples were 20%–30% solutions by weight in CDCl$_3$ with 1% TMS as internal standard; chemical shifts are reported in p.p.m. vs. TMS ($\delta$). Melting points were determined on a Fisher-Johns apparatus and were uncorrected. The melting points of moisture-sensitive compounds were determined in sealed capillaries on an Electrothermal melting point apparatus. Elemental analyses were performed by Gailbraith Laboratories, Knoxville, Tennessee. Because these compounds are moisture-sensitive, all operations with these compounds were carried out under an atmosphere of dry nitrogen. All solvents and reactants used in this work were dried by standard methods and freshly distilled under nitrogen or vacuum prior to use. Solution viscosities were obtained in chloroform at 20° using a Cannon-Ubbelholde viscometer. All temperatures are in degrees Celsius.

1.

(A) PcSiCl$_2$

Silicon tetrachloride (150 g.0.883 mol) was allowed to react with 1,3 diiminoisoindoline (88 g.0.607 mol) in 300 ml of tributylamine and 700 ml of tetralin at reflux for two hrs. The purple crystalline product (73.8 g. 0.120 mol, 80% based on 1,3-diiminoisoindoline) was identified as PcSiCl$_2$ by ir and elemental analysis.

2.

(B) PcSi(OH)$_2$

The basic hydrolysis of PcSiCl$_2$ to PcSi(OH)$_2$ was carried out as previously described. In a 2 l flask, PcSiCl$_2$ (44.0 g, 71.7 mmol), NaOH (11 g, 275 mmol), H$_2$O (1 l), and pyridine (260 ml) were refluxed for one hour. The product (41.2 g, 71.7 mmol, 100%) was recovered by filtration, washed with water, and dried in vacuo. The compound was identified as PcSi(OH)$_2$ by its ir spectrum and elemental analysis.

3.

(C) PcSi(OSiR'PhCl)$_2$ wherein R' is methyl group

PcSi(OH)$_2$ (13.50 g, 46.8 mmol) was placed in a 500 ml 3-neck flask along with a magnetic stir bar. The flask was fitted with a serum cap, an inlet for dry nitrogen gas, and a gas outlet tube and bubbler. The flask was then thoroughly purged with dry nitrogen. While a gentle nitrogen purge was maintained, 225 ml of pyridine and 36 ml of tributylamine were added to the flask. Finally, methylphenyldichlorosilane (25 ml, 160 mmol) was injected into the reaction flask with a syringe. A slow nitrogen purge was maintained as the mixture was stirred at room temperature for eight days. The solution was then filtered and the solid obtained was dissolved in 1.2 l boiling toluene. The hot solution was filtered to remove unreacted PcSi(OH)$_2$. The filtrate was reduced to about 800 ml by continued boiling and finally cooled at 0° for 24 hrs. The product, PcSi(OSiMePhCl)$_2$, (C) which separated as lustrous dark purple needles (14.93 g, 16.89 mmol, 72.2%) was removed by filtration, washed with 100 ml dry heptane, and vacuum dried. The melting point of freshly recrystallized compound C is 292–3°, but the compound was sensitive to atmospheric moisture and would slowly hydrolyze in air (m.p. after 7 days was 282°). The bands in the ir spectrum of compound C are: 1611w, 1523m, 1475m, 1430s, 1337vs, 1294, 1260m, 1169m 1125vs, 1045vs(broad), 915m, 785w, 765m, 735vs, 700m, 571m, 531m, 500m (Si—Cl stretch), 475w, 427w.

ANAL. Calcd for C$_{46}$H$_{32}$N$_8$O$_2$Si$_3$Cl$_2$: C, 62.50; H, 3.65. Found, C, 63.58, H, 4.03.

4.

(D) PcSi(OSiR'PhOH)$_2$ where R' is a methyl group

Crystals of compound C (14.93 g, 16.98 mmol) were placed in a 250 ml flask along with 150 ml of dioxane, 6 ml of pyridine, 6 ml of water, and a magnetic stir bar. After stirring overnight at ambient temperature, the solution was poured slowly into 2.5 l of rapidly stirred water. The blue solid, PcSi(OSiMePhOH)$_2$ compound (D) was removed by filtration and dried at 100° C (14.15 g, 16.70 mmol, 98.9%, m.p. >380°). The bands in the ir spectrum of Compound (D) are: 3430w (broad, 3062w, 1612w, 1593w, 1522m, 1464w, 1432m 1357w, 1338vs, 1296s, 1262m, 1173m, 1128s, 1087s, 1052s, 919m, 860w, 768m, 744s, 706w, 578m, 538m 483w, 432w, 419w, 320vw.

ANAL. Calcd for C$_{46}$H$_{34}$N$_8$O$_4$Si$_3$: C, 65.22; H, 4.05; Si, 9.95. Found, C, 65.31; H, 4.18; Si, 10.11.

5.

(E) PcSi(OSiR$^1$PhOSiR$_2^2$Cl)$_2$ wherein R$^1$ and R$^2$ are methyl groups

Dimethylidichlorosilane(0.28 g, 2.47 mmol), 25 ml of benzene, and 0.5 ml of dry pyridine were placed in a 100 ml 3-neck flask equipped with a nitrogen gas inlet, drying tube outlet, stopper, and magnetic stir bar. With a nitrogen purge, a solid addition tube containing compound D, PcSi(OSiMePhOH)$_2$, (1.00 g, 1.18 mmol) was substituted for the stopper. While the solution was stirred, small amounts of compound D were gradually added to the reaction mixture. Preliminary nmr experiments revealed that the reaction between compound D and dimethyldichlorosilane in the presence of pyridine was quite rapid. The product of this reaction, PcSi(DSiMePhOSiMe$_2$Cl)$_2$, was observed via nmr spectroscopy but the compound was not isolated.

6.

(F) PcSi(OSiR$^1$PhOSiR$_2{}^2$OH)$_2$ wherein R$^1$ and R$^2$ are methyl groups.

After stirring for 20 min at room temperature, 3 ml of water was added to the reaction mixture of reaction 5 and the mixture stirred another hour. The reaction mixture was extracted with 50 ml of water, and the organic phase was collected and allowed to evaporate in the hood. The residue was dissolved in 5–10 ml of dichloromethane and added dropwise to 200 ml of stirred ligroin. After the solution had partly evaporated, some solid material precipitated. This solid was removed by filtration and the filtrate was allowed to evaporate slowly over a period 1–2 days. Small dark purple crystals of PcSi(OSiMePhOSiMe$_2$OH)$_2$, (F) (0.69 g, 0.69 mmol, 58.5%, m.p. 168–9°) were deposited. It should be noted that compound F was difficult to obtain pure due to the presence of side products of similar solubility. The bands in the ir spectrum of compound F are: 3440w, 3078w, 2968w, 2599w, 1615w, 1594w, 1526s, 1477m, 1435s, 1360m, 1340vs, 1298s, 1263s, 1172m, 1128vs, 1087vs, 1033vs (broad), 920m, 885w, 792m, 769m, 740vs, 707m, 576m, 533m, 479w, 430w, ANAL. Calcd for C$_{50}$H$_{46}$N$_8$O$_6$Si$_5$: C, 60.33; H, 4.66; Si, 14.11. Found, C, 60.47; H, 4.70: Si, 13.98.

7.

G-0 UrR$_2{}^3$Si(OSiR$_2{}^4$)$_q$Ur wherein R$^3$ is a methyl group and q equals 0.

This compound was synthesized in a two-step process. A 5 l 3-neck flask was equipped with a mechanical stirrer, a 250 ml pressure equalizing dropping funnel, and a low temperature condenser with an outlet to the atmosphere through a drying tube. In place of a stopper, the top of the dropping funnel was fitted with an inlet for dry nitrogen gas. A brisk nitrogen purge of the apparatus was maintained for thirty minutes before 1.3 l of ethyl ether and two moles of butyl lithium (2.4 M in hexane) were added to the flask. The flask was cooled in an ice bath and dry ice and acetone were added to the low temperature condenser. Pyrrolidine (142 g, 2 mol) was placed in the dropping funnel and added dropwise with stirring to the lithio solution. After the pyrrolidine addition, dimethyldichlorosilane (129.1 g, 1 mol) was placed in the dropping funnel and added to the lithio solution. The cooling baths and nitrogen purge were maintained until all the dimethyldichlorosilane had been added. The reaction mixture was allowed to reach room temperature and stirred overnight under nitrogen. Following removal of lithium chloride by filtration under nitrogen the product, bis(pyrrolidinyl)dimethylsilane, was obtained by fractional distillation. (153.5 g 0.774 mol, 77%, b.p., 105°/15.5 mm). Bis(pyrrolidinyl)dimethylsilane (55.0 g, 0.278 mol) and ethyl ether (150 ml) were placed in a 500 ml flask fitted with a nitrogen gas inlet, a mechanical stirrer, and a dropping funnel with a drying tube gas outlet. A nitrogen purge was maintained throughout the course of the reaction. The flask was cooled with an ice bath and phenyl isocyanate (66.2 g, 0.556 mol) was placed in the dropping funnel and added dropwise to the stirred solution. When addition of the phenyl isocyanate was nearly complete, a white solid began to crystallize. The mixture was allowed to warm slowly to room temperature and stirred overnight. The solid was removed by filtration under nitrogen and dried under vacuum. The product (85.0 g, 0.195 mol, 70%) was recrystallized to constant mp. (107°) from dichloromethaneether. An nmr spectrum of the recrystallized product showed an aromatic multiplet (10H, Ph) at about 7.02, triplet (8H, Py 2,5) at 2.90 a triplet (8H, Py 3,4) at 1.59 and a sharp singlet (6H, Si$_1$) at 0.40. From the nmr spectrum, the purity of compound G-O was judged to be 95% with the only impurity being the urea, HNPhC(O)NC$_4$H$_8$.

8.

G-1 UrR$_2{}^3$Si(OSiR$_2{}^4$)$_q$Ur wherein R$^3$ and R$^4$ are methyl groups and q equals 1.
1,3-Bis(N-pyrrolidine-N'-phenylureido)tetramethyldisiloxane.

The intermediate compound in the synthesis of compound G-1 1,3-bis(Pyrrolidinyl)-tetramethyldisiloxane(b.p., 145°/21 mm, 60% yield) was prepared by direct reaction of 1,3-(dichloro)tetramethyldisiloxane with pyrrolidine in heptane solvent. The nmr spectrum of this colorless liquid intermediate (neat with internal TMS) showed a triplet (8H,Py$_{2,5}$) at $\delta$ 2.98, a triplet (8H, Py$_{3,4}$) at 1.67 and a sharp singlet (12H,Si$_1$) at 0.04. Following the same procedure described for G-O above, the addition of phenyl isocyanate to bis(pyrrolidinyl) tetramethyldisiloxane resulted in the formation of the solid, compound (G-1), (m.p., 105°), in 81% yield. The similar solubilities of compound (G-1) and urea impurity (identified by nmr as HNPhC(O)NC$_4$H$_8$ made it impossible to obtain this compound pure even after several recrystallizations from toluene. The nmr spectrum of compound G-1 showed a multiplet (10H, Ph) at $\delta$ 7.10 a triplet (8H, py$_{2,5}$) at 2.97, a triplet (8HPy$_{3,4}$) at 1.63 and a sharp singlet (12H, Si$_1$) at 0.08. The nmr spectrum indicated that compound (G-1) was obtained in 93% purity.

9.

H-1 PcSi(OSiR$^1$Ph(OSiR$_2{}^2$)$_p$O(SiR$_2{}^4$O)$_q$SiR$_2{}^3$Ur)$_2$ where R$^1$, R$^2$, R$^3$, and R$^4$ are methyl groups and p equals 1 and q equals 1.

Compound H-1 was prepared by the addition of one-half mole equivalent of PcSi disilanol (F) to one mole equivalent of bis(ureido)silane G-0 in CDCl$_3$. The reaction was monitored by $^1$H nmr spectroscopy. Ten minutes after mixing (F) and G-0 peaks for disilanol (F) were absent indicating rapid reaction of (F) with (G-0). Three new high field absorptions in a 2:2:1 relative intensity indicated the presence of H-1. In the absence of reactive hydroxy groups compound H-1 is stable in solution for days. Other polar aprotic solvents such as CH$_2$Cl$_2$, CHCl$_3$ (CHCl$_2$)$_2$ and (CH$_2$Cl)$_2$ could be used for the preparation of H-1. If exposed to the atmosphere compound H-1 would react rapidly with water to give the corresponding disilanol. Compound H-1 can also be prepared from the reaction of disilanol (D) with bis-(ureido)disiloxane G-1 (equation 6, p equals 0, q equals 1, $R^1$, $R^3$ and $R^4$ are methyl groups).

10.

H-2    $PcSi(OSiR^1Ph(OSiR_2^2)_pO(SiR_2^4)_qSiR_2^3Ur)_2$
where $R^1$, $R^2$, $R^3$ and $R^4$ are methyl groups and p equals 1 and q equals 1.

Compound H-2 was prepared by the addition of one-half mole equivalent of PcSi disilanol (F) to one mole equivalent of bis(ureido)disiloxane (G-1 ) in $CHCl_3$ (equation 6, p equals 1, q equals 1, $R^1$, $R^2$, $R^3$, and $R^4$ are methyl groups). The reaction was monitored by $^1H$ nmr spectroscopy. Within two minutes the $^1H$ nmr spectrum of the solution showed that H-2 had been produced, essentially quantitatively, as for H-1. Other polar non-hydroxylic solvents could be used for this reaction, e.g., $CHCl_3$, $CH_2Cl_2$, $(CHCl_2)_2$ and $(CH_2Cl)_2$. Compound H-2 was stable in solution in the absence of hydroxylic reagents. It reacted readily with water to give the corresponding disilanol.

The bis(ureido)siloxanephthalocyanine monomers of the present invention readily react with the novel disilanols of the invention to form silicon-phthalocyanine siloxane polymers of U.S. Patent Application Ser. No. 880,514 of Kenneth J. Wynne and John B. Davison for Silicon-Phthalocyanine-Siloxane Polymers filed Feb. 23, 1978. This application is herein incorporated by reference.

The high reactivity with hydroxylic groups of the bis (ureido) siloxane phthalocyanine monomers of the present invention, their stability to self condensation in situ together with the intense color and high thermal stability of Pc siloxane groups make the monomers of the present invention attractive candidates as dyes for high temperature polymers or coatings. The high thermal stability of the Pc siloxane dye would not compromise the thermal stability of the substrate to at least 300° C in air.

Obviously many modifications and variations of the present invention are possible in light of the above teachings. It is therefore to be understood that within the scope of the appended claims the invention may be practiced otherwise than as specifically described.

What is claimed and desired to be secured by letters patent of the Unites States is:

1. A silicon-phthalocyanine-siloxy monomer having the formula:

wherein R' and R" are alkyl groups having from 1 to 8 carbon atoms, r is an integer from 1 to 4, and x is a hydroxyl group or an ureido group having the formula:

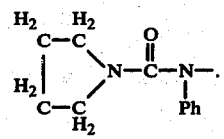

2. The monomer of claim 1 wherein R' and R" are alkyl groups having from 1 to 3 carbon atoms.

3. The monomer of claim 1 where r is 2 or 3.

4. The monomer of claim 3 wherein R' and R" are methyl groups.

5. The monomer of claim 3 wherein R' and R" are ethyl groups.

6. The monomer of claim 2 wherein r is 1 .

* * * * *